US00PP19629P2

(12) United States Plant Patent
Wain

(10) Patent No.: US PP19,629 P2
(45) Date of Patent: Jan. 20, 2009

(54) ***CHRYSANTHEMUM* PLANT NAMED 'YOGREEN VALLEY'**

(50) Latin Name: *Chrysanthemum×morifolium*
Varietal Denomination: Yogreen Valley

(75) Inventor: Peter Wain, Southampton (GB)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 12/006,789

(22) Filed: Jan. 3, 2008

(51) Int. Cl.
*A01H 5/00* (2006.01)

(52) U.S. Cl. ..... Plt./286
(58) Field of Classification Search ..... Plt./286
See application file for complete search history.

*Primary Examiner*—Annette H Para
*Assistant Examiner*—S. B. McCormick-Ewoldt
(74) *Attorney, Agent, or Firm*—C. A. Whealy

(57) ABSTRACT

A new and distinct cultivar of *Chrysanthemum* plant named 'Yogreen Valley', characterized by upright and uniformly mounded plant habit; freely branching habit; uniform flowering response; early flowering habit; daisy-type inflorescences with green-colored quilled ray florets; and good post-production longevity.

1 Drawing Sheet

Botanical designation: *Chrysanthemum×morifolium*
Cultivar Varietal denomination: 'Yogreen Valley'

BACKGROUND OF THE INVENTION

The present invention relates to a new and distinct cultivar of *Chrysanthemum* plant, botanically known as *Chrysanthemum×morifolium* plant, commercially grown as a pot-type *Chrysanthemum* and hereinafter referred to by the name 'Yogreen Valley'.

The objective of the breeding program is to create new pot-type *Chrysanthemum* cultivars that are suitable for year-round production with uniform plant growth habit, freely branching habit, good vigor, desirable inflorescence form and floret colors, fast response time and good postproduction longevity.

The new *Chrysanthemum* originated from a cross-pollination made by the Inventor in January, 2004, in Fareham, Hampshire, United Kingdom of a proprietary selection of *Chrysanthemum×morifolium* identified as code number P888G 3, not patented, as the female, or seed, parent with a proprietary selection of *Chrysanthemum×morifolium* identified as code number P806G 1, not patented, as the male, or pollen, parent. The new *Chrysanthemum* was discovered and selected by the Inventor as a single flowering plant within the progeny of the stated cross-pollination in a controlled environment in Fareham, Hampshire, United Kingdom. The selection of this plant was based on its uniform plant growth habit, freely Branching habit, good vigor, desirable inflorescence form and floret coloration, fast response time and good postproduction longevity.

Asexual reproduction of the new *Chrysanthemum* by vegetative tip cuttings was first conducted in Fareham, Hampshire, United Kingdom in December, 2004. Asexual reproduction by cuttings has shown that the unique features of this new *Chrysanthemum* are stable and reproduced true to type in successive generations.

SUMMARY OF THE INVENTION

Plants of the cultivar Yogreen Valley have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yogreen Valley'. These characteristics in combination distinguish 'Yogreen Valley' as a new and distinct potted *Chrysanthemum* cultivar:

1. Upright and uniformly mounded plant habit.
2. Freely branching habit.
3. Uniform flowering response.
4. Can be grown center-budded or as natural spray type.
5. Early flowering habit, eight-week response time.
6. Daisy-type inflorescences with green-colored quilled ray florets.
7. Good postproduction longevity with plants maintaining good substance and color for about three weeks in an interior environment.

Plants of the new *Chrysanthemum* differ from plants of the female parent selection in the following characteristics:

1. Plants of the new *Chrysanthemum* are larger than plants of the female parent selection.
2. Inflorescences of plants of the new *Chrysanthemum* are larger than inflorescences of plants of the female parent selection.
3. Plants of the new *Chrysanthemum* flower about four days later than plants of the female parent selection.

Plants of the new *Chrysanthemum* differ from plants of the male parent selection in the following characteristics:

1. Plants of the new *Chrysanthemum* and the male parent selection differ in ray floret color as plants of the male parent selection have yellow-colored ray florets.
2. Inflorescences of plants of the new *Chrysanthemum* are smaller than inflorescences of plants of the male parent selection.
3. Plants of the new *Chrysanthemum* flower about four days later than plants of the male parent selection.

Plants of the new *Chrysanthemum* can be compared to plants of the *Chrysanthemum* cultivar Yokilleen, disclosed in U.S. Plant Pat. No. 17,862. In side-by-side comparisons conducted in Fareham, Hampshire, United Kingdom, plants of the new *Chrysanthemum* differed from plants of the cultivar Yokilleen in the following characteristics:

1. Plants of the new *Chrysanthemum* were larger than plants of the cultivar Yokilleen.
2. Inflorescences of plants of the new *Chrysanthemum* were larger than inflorescences of plants of the cultivar Yokilleen.
3. Plants of the new *Chrysanthemum* flowered about four days later than plants of the cultivar Yokilleen.

BRIEF DESCRIPTION OF THE PHOTOGRAPH

The accompanying photograph illustrates the overall appearance of the new *Chrysanthemum*. These photograph shows the colors as true as it is reasonably possible to obtain in colored reproductions of this type. Colors in the photograph may differ slightly from the color values cited in the detailed botanical description which accurately describe the colors of the new *Chrysanthemum*. The photograph comprises a side perspective view of typical flowering plants of 'Yogreen Valley' grown in a container.

DETAILED BOTANICAL DESCRIPTION

The aforementioned photograph and following observations and measurements describe plants grown in Leamington, Ontario, Canada during the autumn in a fiberglass-covered greenhouse and under conditions and practices which approximate those generally used in commercial pot-type *Chrysanthemum* production. During the production of the plants, day temperatures ranged from 21° C. to 27° C., night temperatures ranged from 17° C. to 19° C. and light levels ranged from 5,000 to 6,000 foot candles. Four unrooted cuttings were directly stuck in 15-containers, exposed to long day/short night conditions, and pinched about two weeks later. One week after the pinch, the photoinductive short day/long night treatments were started. Plants used in the photograph and for the desciption were disbudded and were about two months old. In the following description, color references are made to The Royal Horticultural Society Colour Chart, 1995 Edition, except where general terms of ordinary dictionary significance are used.

Botanical classification: *Chrysanthemum×morifolium* cultivar Yogreen Valley.

Parentage:

*Female, or seed, parent—Proprietary selection of Chrysanthemum×morifolium* identified as code number P888G 3, not patented. Male, or pollen, parent: Proprietary selection of *Chrysanthemum×moricolium* identified as code number P806G 1, not patented.

Propagation:

*Type*.—Terminal vegetative cuttings.

*Time to initiate roots*.—About four days at temperatures of about 21° C.

*Time to produce a rooted young plant*.—About ten days at temperatures of about 21° C.

*Root description*.—Medium thickness, fibrous; white in color.

*Rooting habit*.—Freely branching; moderately dense.

Plant description:

*Appearance*.—Herbaceous daisy pot-type *Chrysanthemum* typically grown as a center-budded or as a natural spray type. Stems upright and outwardly spreading giving a uniformly mounded appearance to the plant. Freely branching habit, about four lateral branches develop after removal of terminal apex (pinching); dense and full plant habit; moderately vigorous growth habit.

*Plant height*.—About 29 cm.

*Plant width*.—About 45 cm.

*Lateral branches* (*peduncles*): Length: About 24 cm. Diameter: About 6 mm. Internode length: About 3.3 cm. Strength: Very strong. Texture: Pubescent. Color: Close to 144A.

Foliage description:

*Arrangement*.—Alternate, simple.

*Length*.—About 7.5 cm.

*Width*.—About 5.75 cm.

*Shape*. —Palmately lobed.

*Apex*.—Mucronate.

*Base*.—Attenuate with truncate tendencies.

*Margin*.—Palmately lobed, sinuses between lateral lobes parallel to divergent.

*Texture, upper and lower surface*.—Pubescent.

*Color*.—Developing and fully expanded foliage, upper surface: Lighter green than 147A; venation, close to 147B. Developing and fully expanded foliage, lower surface: Close to 147B; venation, close to 147B.

*Petiole length*.—About 1.5 cm.

*Petiole diameter*.—About 4 mm.

*Petiole texture, upper and lower surfaces*.—Pubescent.

*Petiole color, upper surface*.—Center, close to 147B to 147C; towards the margins, lighter green that 147A.

*Petiole color, lower surface*.—Close to 147B.

Inflorescence description:

*Appearance*.—Daisy-type inflorescence form with quilled ray florets. Inflorescences borne on terminals above foliage. Disk and ray florets arranged acropetally on a capitulum. Inflorescence not fragrant. Typically grown as a center-budded type or as a natural spray.

*Flowering response*.—Under natural conditions, plants flower in the autumn/winter in the Northern Hemisphere. At other times of the year, inflorescence initiation and development can be induced under short day/long night conditions (at least 13.5 hours of darkness). Early flowering habits; plants exposed to three weeks of long day/short night conditions followed by photoinductive short day/long night conditions flower about 54 days later.

*Postproduction longevity*.—Inflorescences maintain good color and substance for about three weeks in an interior environment.

*Quantity of inflorescences per lateral stem*.—About seven.

*Inflorescence bud*.—Height: About 7 mm. Diameter: About 9 mm. Shape: Oblate. Color: Close to 138A.

*Inflorescence size*.—Diameter: About 5.5 cm. Depth (height): About 1.8 cm. Disc diameter: About 1.5 cm. Receptacle height: About 5 mm. Receptacle diameter: About 7 mm. Receptacle color: Close to 144A.

*Ray florets*.—Shape: Quilled. Orientation: Initially upright, then about 70° from vertical. Length: About 2.9 cm. Width: Towards the apex, about 4 mm; towards the base, about 1.5 mm. Apex: Emarginate, acute of obtuse. Base: Fused. Margin: Entire. Texture, upper and lower surfaces: Smooth, glabrous, satiny. Number of ray florets per inflorescence: About 115 arranged in about five whorls. Color: When opening and fully opened, upper surface: Close to 145A; color becoming closer to 145B to 145C with development. When opening and fully opened, lower surface: Close to 145A; color becoming closer to 145B to 145C with development.

*Disc florets*.—Arrangement; massed at center of receptacle. Shape: Tubular, elongated. Apex: Five-pointed. Length: About 1 cm. Width: Towards the apex, about 3 mm; towards the base, about 1 mm. Numbers of disc florets per inflorescence: About 67. Color, immature: Apex: Close to 154A. Mid-section: Close to 145A. Base: Close to 155D. Color, mature: Apex: Close to 6A. Mid-section: Close to 145A. Base Close to 155D.

*Phyllaries*.—Number of phyllaries per inflorescence: About 16 arranged in two whorls. Length: About 1 cm. Width: About 4 mm. Shape: Lanceolate. Apex: Acute. Base: Truncate. Texture, upper surface: Smooth, waxy. Texture, lower surface: Pubescent. Color, upper surface: Close to 144A. Color, lower surface: Close to 138A.

*Peduncles*.—Length: First peduncle: About 2.6 cm. Fourth peduncle: About 5.2 cm. Seventh peduncle: About 5.5 cm. Diameter (first peduncle): About 2.5 mm. Angle: About 45° from vertical. Strength: Strong, flexible. Texture: Pubescent. Color: Close to 144A.

*Reproductive organs*.—Androecium: Present on disc florets only. Filament length: About 7 mm. Filament color: Close to 155D. Anther shape: Narrowly oblong. Anther length: Less than 1 mm. Anther color: Close to 5A. Pollen amount: None observed. Gynoecium: Pistil length: About 1.1 cm. Stigma shape: Bi-parted. Stigma color: Close to 9A. Style length: About 9 mm. Style color: Close to 155D. Ovary color: Close to 155D.

*Seed/fruit*.—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* have been observed to tolerate temperatures ranging from about 1° C. to about 35° C.

It is claimed:

1. A new and distinct *Chrysanthemum* plant named 'Yogreen Valley' as illustrated and described.

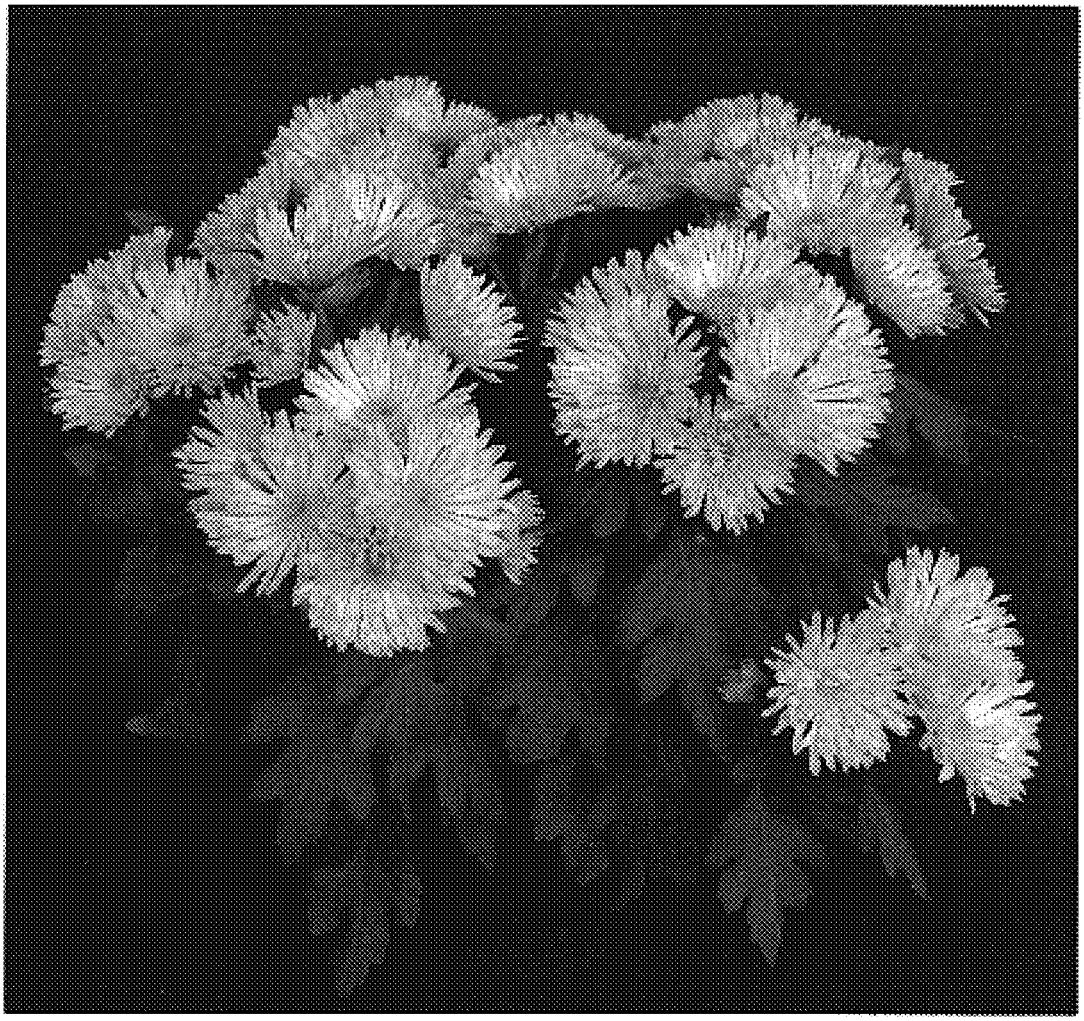

* * * * *